United States Patent
Berlinger et al.

(10) Patent No.: US 11,794,035 B2
(45) Date of Patent: Oct. 24, 2023

(54) TRIGGERING OF X-RAY-IMAGES BASED ON SURFACE MEASUREMENTS

(71) Applicant: Brainlab AG, Munich (DE)

(72) Inventors: Kajetan Berlinger, Munich (DE); Hagen Kaiser, Icking (DE); Michael Stead, Munich (DE)

(73) Assignee: Brainlab AG, Munich (DE)

( * ) Notice: Subject to any disclaimer, the term of this patent is extended or adjusted under 35 U.S.C. 154(b) by 514 days.

(21) Appl. No.: 17/046,077

(22) PCT Filed: Aug. 13, 2019

(86) PCT No.: PCT/EP2019/071660
§ 371 (c)(1),
(2) Date: Oct. 8, 2020

(87) PCT Pub. No.: WO2021/028022
PCT Pub. Date: Feb. 18, 2021

(65) Prior Publication Data
US 2023/0145557 A1  May 11, 2023

(51) Int. Cl.
*A61N 5/10* (2006.01)
*A61B 6/00* (2006.01)

(52) U.S. Cl.
CPC ............ *A61N 5/1049* (2013.01); *A61B 6/488* (2013.01); *A61N 2005/1059* (2013.01)

(58) Field of Classification Search
CPC .......... A61N 5/1049; A61N 2005/1059; A61N 2005/1054; A61N 2005/1061; A61B 6/488; A61B 6/08; A61B 6/589
See application file for complete search history.

(56) References Cited

U.S. PATENT DOCUMENTS

| | | | |
|---|---|---|---|
| 9,149,655 B2 | 10/2015 | Vilsmeier et al. | |
| 2003/0099328 A1 | 5/2003 | Jensen | |
| 2012/0001085 A1 | 1/2012 | Fujimoto | |
| 2014/0371513 A1 | 12/2014 | Maurer, Jr. | |
| 2016/0374639 A1 | 12/2016 | Becker | |
| 2018/0268558 A1* | 9/2018 | Bauer | G06T 7/254 |

FOREIGN PATENT DOCUMENTS

| EP | 3247457 A1 | 11/2017 |
|---|---|---|
| WO | 2019/238220 A1 | 12/2019 |

OTHER PUBLICATIONS

International Search Report and Written Opinion for corresponding International Application No. PCT/EP2019/071660, dated May 7, 2020. 10 pages.

* cited by examiner

*Primary Examiner* — Courtney D Thomas
(74) *Attorney, Agent, or Firm* — Tucker Ellis LLP (57) ABSTRACT

The present invention relates to a computer-implemented medical method for monitoring a spatial position of a patient's body part, wherein at least one optimum spatial direction for a line of sight of a check x-ray-image is determined, that qualifies for quantifying a deviation of the spatial position of the patient's body part from a target spatial position for the patient's body part. The present invention further relates to a corresponding computer program and a corresponding medical system.

16 Claims, 4 Drawing Sheets

TRIGGERING OF X-RAY-IMAGES BASED ON SURFACE MEASUREMENTS

RELATED APPLICATION DATA

This application is a national phase application of International Application No. PCT/EP2019/071660 filed Aug. 13, 2019, the contents of which are incorporated herein by reference.

FIELD OF THE INVENTION

The present invention relates to a computer-implemented method for monitoring a spatial position of a patient's body part, a corresponding computer program, a program storage medium storing such a program and a computer for executing the program, as well as a medical system comprising an electronic data storage device and the aforementioned computer.

TECHNICAL BACKGROUND

Image-guided radiotherapy (IGRT) procedures usually utilize x-ray-images in order to make sure that a patient is in the correct position for radiotherapy, which means that a pathological structure of the patient to be irradiated is correctly positioned with respect to a radiation treatment apparatus such that the intended treatment radiation dose can be applied to the pathological structure. Usually, one or more x-ray-images are made once the patient has been placed in a presumably correct position with respect to the radiation treatment apparatus, and checked against previously acquired scans on which basis the treatment has been planned. For example, such check x-ray-images are acquired with one or more x-ray-apparatus which can be either installed in the treatment room at a fixed spatial position, but there are also systems which provide an x-ray-apparatus at the gantry of the radiation treatment apparatus, which therefore rotates around the patient together with the treatment beam source. In order to ensure that the pathological structure maintains its correct position throughout the entire duration of the treatment procedure, further x-ray-images are made from time to time which are then checked again against the planning scan for determining whether the pathological structure is still in the correct position or whether it is necessary to re-position the patient or re-adjust the treatment beam.

It is a frequent practice to trigger the acquisition of such check x-ray-images as a function of the gantry angle of the radiation treatment apparatus, i.e. the angle of the treatment beam(s) with respect to the patient, as a function of the treatment radiation dose applied so far to the patient and the pathological structure, or as a function of the treatment progress. In other words, the acquisition of check x-ray-images is usually triggered at predefined time intervals or predefined occasions that occur during the cause of the treatment procedure.

On the other hand, the patient, or to be more precise, the pathological structure may move away from the planned position in many unpredictable ways. Thus, previous approaches of triggering the acquisition of check x-ray-images as a function of predefined occasions or time intervals cannot ensure that, if a positional deviation of the pathological structure occurs, that this deviation can be properly quantified on the basis of the x-ray-images acquired. For example, it is difficult to quantify a positional deviation of the pathological structure the direction of which includes a significant component in the direction in which the check x-ray-image has been taken. In case the pathological structure has moved exactly or almost parallel to the direction the check x-ray-image has been taken in, it is very difficult to even tell whether the structure has moved at all, but it is surely impossible to quantify by which amount the structure has moved, which information is of course necessary for re-adjusting the treatment beam(s) or for re-positioning the patient in order to pursue the treatment as planned. Of course, increasing the frequency in which check x-ray-images are acquired will increase the chance that, if a positional deviation occurs, one or more images are acquired in a direction that has a significant component perpendicular to the direction of motion of the pathological structure. However, this comes along with unwanted additional radiation exposure to the patient. Thus, a compromise has to be found between a safe and reliable monitoring of the patient's position during radiotherapy, and the lowest possible radiation exposure to the patient.

The present invention has the object of providing an approach of monitoring the patient's position during radiotherapy with a significantly reduced radiation dose for the patient, but without compromising the reliability of the positional monitoring.

The present invention can be used for image-guided radiotherapy procedures e.g. in connection with a system for image-guided radiotherapy such as VERO® and ExecTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present invention relates to an approach of monitoring the spatial position of a patient's body part during radiotherapy, wherein a possible positional deviation of a pathological structure to be irradiated is quantified with the help of x-ray-images the acquisition of which is triggered on the basis of positional measurements of the surface of the patient's body, that show the spatial direction in which the positional deviation has occurred.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of monitoring a spatial position of a patient's body part. The method comprises executing, on at least one processor of at least one computer (for example at least one computer being part of a navigation system), the following exemplary step which are executed by the at least one processor:

surface data is acquired, describing a spatial position of at least a surface section of the patient's body part;

deviation data is acquired based on the surface data, describing that the spatial position of the surface section deviates from a target spatial position for the surface section;

deviation direction data is determined based on the surface data and the deviation data, describing a spatial direction in which the spatial position of the surface section deviates from the target spatial position for the surface section;

check direction data is determined based on the deviation direction data, describing at least one optimum spatial direction for a line of sight of a check x-ray-image that qualifies for quantifying a deviation of the spatial position of the patient's body part from a target spatial position for the patient's body part.

In other words, the spatial position of the patient's skin, in particular the skin of the patient's body part which includes the pathological structure to be irradiated is monitored over time such that, if the patient's body part moves away from it's intended position, it is not only detected that the pathological structure has likely moved, as well, but also in which direction it has most probably moved.

Thus, the necessity to acquire check x-ray-images in relatively short intervals is overcome by the present invention. Even though images may still be made at a (significantly reduced) rate to check whether the pathological structure has moved, it is even possible that check images are only made if the surface measurements show that the patient's body part and presumably also the pathological structure has moved away from its intended position. This alone significantly reduces the radiation exposure to the patient.

The present invention not only allows for reducing the amount of check x-ray-images to an absolute minimum, but also increases the quality of the check x-ray-images in terms of quantifying the amount by which a pathological structure has moved. The precision of image-based measurements for determining how far the pathological structure has moved with respect to the radiation treatment apparatus and the treatment beam(s) strongly depends on the angle between the direction of motion and the image direction, with the best results being acquired from an image taken in a direction that is substantially perpendicular to the direction of motion. In such ideal case, the direction of motion does not have any component parallel to the image direction, which cannot be derived from the image. In order to provide the best results possible, it is therefore the approach of the present invention to determine at least one spatial direction in which a check x-ray-image should be made such that the direction of motion at best does not have a component which cannot be derived from the image, or wherein the amount of such component is at least kept as low as possible.

All in all, the present invention provides an approach for monitoring the spatial position of a patient's body part including a pathological structure with a significantly reduced number of x-ray-images, the usability of which for determining positional deviations is increased at the same time.

For example, the step of acquiring surface data may involve monitoring the spatial position of the surface section via at least one camera adapted for optical surface measurements, and particularly involves at least one of:
- a time-of-flight measurement;
- a structured-light measurement;
- a stereoscopic measurement.

In general, each (optical) measuring technique for determining and monitoring the spatial position of the patient's surface/skin may be used in the context of the present invention. In a more specific example of the present invention, the spatial position of a surface section may be monitored by means of one single optical camera or a camera array having two, three or more optical cameras, which can detect electromagnetic radiation (for example light having a wavelength in the visible and/or infrared range), reflected from the patient's surface. The one or more camera(s) can further maintain their spatial position (spatial location and/or spatial orientation) within the treatment room for at least the duration of the treatment performed on the patient. On the other hand, those cameras may also be installed at a gantry of a radiation treatment apparatus that is adapted to rotate around the patient.

In a further example of the present invention, the spatial direction in which a deviation of the spatial position of the surface section from the target spatial position for the surface section is determined, includes at least one of a direction of a translational deviation and/or an axis of rotation of a rotational deviation. In other words, the present invention may provide for a detection of a translational deviation as well as for a rotational deviation of the patient's body part along with its surface section from their intended position for which the pathological structure to be irradiated takes a position in accordance with the treatment plan.

Thus, in a further example of the present invention, the optimum spatial direction may be defined as being
- substantially perpendicular to the direction of a translational deviation, and/or
- substantially parallel to the axis of rotation of a rotational deviation.

Since a check x-ray-image provides the most valuable information for quantifying a positional deviation if the direction of motion does not have a component which is parallel to the line of sight of the check x-ray-image. Consequently, it is the aim of the present invention to determine an optimum spatial direction which is preferably perpendicular to the direction of the spatial deviation. In case the deviation comprises a translational component as well as a rotational component, a compromise has to be found between the optimum line of sights for the translational and the rotational deviation, respectively. For example, the spatial direction of the overall motion (including one or more translational components and/or one or more rotational components) may serve as the basis for calculating the optimum direction for the check x-ray-image.

In a further example, determining check direction data involves determining a range of acceptance around the at least one optimum spatial direction, which defines an upper limit for an angle enclosed by the optimum spatial direction and an acceptable spatial direction for a line of sight of a check image. Since the optimum spatial direction for the check image calculated for a specific spatial deviation may, in some cases, not be reached at all, or for other cases, cannot be reached by the x-ray-apparatus in an efficient manner, for example due to geometrical and/or mechanical limitations of the x-ray-apparatus, a certain range of acceptance can be defined for the spatial direction of the check image's line of sight, for which a check image still delivers satisfying results for quantifying the spatial deviation of the pathological structure. Such range of acceptance may be set automatically by the system/software or manually by the user.

In still another example, the inventive method may further include the following steps:

acquiring imager direction data describing the current spatial direction of a line of sight of an x-ray imaging device which is adapted to provide the check image;

generating, based on the check direction data and the imager direction data, a triggering signal for the x-ray imaging device to acquire a check image in the optimum spatial direction or at least within the range of acceptance.

Once the optimum spatial direction or the range of acceptance for a spatial direction for the line of sight of a check x-ray-image has been calculated, the at least one x-ray-imaging device can be correspondingly controlled to acquire the check image in the desired direction. In order to do so, the current imaging direction of the x-ray-apparatus has to be known and, for movable x-ray-apparatus, be monitored over time, such that when the current imaging direction coincides with the optimum direction or at least lies within the range of acceptance, an acquisition of a check x-ray-image is triggered.

In one specific example of the present invention, the x-ray imaging device includes a plurality (two, three or more) of x-ray imaging devices, which in particular have lines of sight which intersect each other at an angle.

In such case, the inventive method may comprise the step of generating a triggering signal including selecting, from the plurality of x-ray-imaging devices, an x-ray imaging device having a line of sight which is closest to, is within or will at first reach the optimum spatial direction or at least the range of acceptance, such that the check x-ray-image is acquired via the selected imaging device.

Further, the x-ray-imaging device may further be movable with respect to the patient's body part, particularly along a circumferential pathway around the patient's body part, specifically together with a treatment beam device. In such case, the x-ray imaging device may even be a monoscopic imaging device having a single radiation source and a single radiation emitter. Further, the imaging device may, in a specific example, be stalled at the gantry of a radiation treatment apparatus and may therefore rotate around the patient to be treated.

While the above described approaches to trigger the acquisition of a check x-ray-image only when an optimum or at least acceptable spatial position is reached, it may for some cases be desirable that further check images are acquired. Thus, a triggering signal for acquiring a check x-ray image may also be set off in a conventional manner known from the prior art, i.e. depending on at least one of:

the relative position between a radiation treatment apparatus and the patient's body part;
a dose of radiation applied to the patient's body part;
the elapsed radiation treatment time.

Consequently, further check x-ray-images can be acquired in addition to the ones acquired in a preferred spatial direction.

In another example of the present invention, generating the triggering signal may include changing the relative position of the patient's body part and the x-ray imaging device such that the line of sight of the x-ray imaging device substantially coincides with the optimum spatial direction or is at least within the range of acceptance, particularly by moving at least one of a patient support limit and the x-ray imaging device. Provided that the patient support unit along with the patient couch and/or the x-ray imaging device(s) are movable and can therefore change their position relative to each other, the imaging direction of the x-ray apparatus can be changed for at least the time which is necessary to acquire the check x-ray image.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:

a) the at least one computer according to the fourth aspect;
b) a camera adapted for optical surface measurements; and
c) a x-ray imaging device for providing at least one x-ray-check image of the patient's body part,
wherein the at least one computer is operably coupled to the camera for determining check direction data; and
the x-ray imaging device for issuing a control signal to the x-ray imaging device for controlling the operation of the x-ray imaging device on the basis of the check direction data.

Alternatively or additionally, the invention according to the fifth aspect is directed to a for example non-transitory computer-readable program storage medium storing a program for causing the computer according to the fourth aspect to execute the data processing steps of the method according to the first aspect.

In an example of the system according to the fifth aspect, the medical device comprises a radiation treatment apparatus comprising a treatment beam source and a patient support unit (such as at least one of a patient bed or a headrest). The at least one computer is then operably coupled to the x-ray imaging device for issuing a control signal to the x-ray imaging device for controlling, on the basis of the check direction data, at least one of
- the operation of the x-ray imaging device or
- the position of the patient support unit.

For example, the invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity.

The present invention also relates to the use of the device/system or any embodiment thereof for monitoring a spatial position of a patient's body part during radiotherapy.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
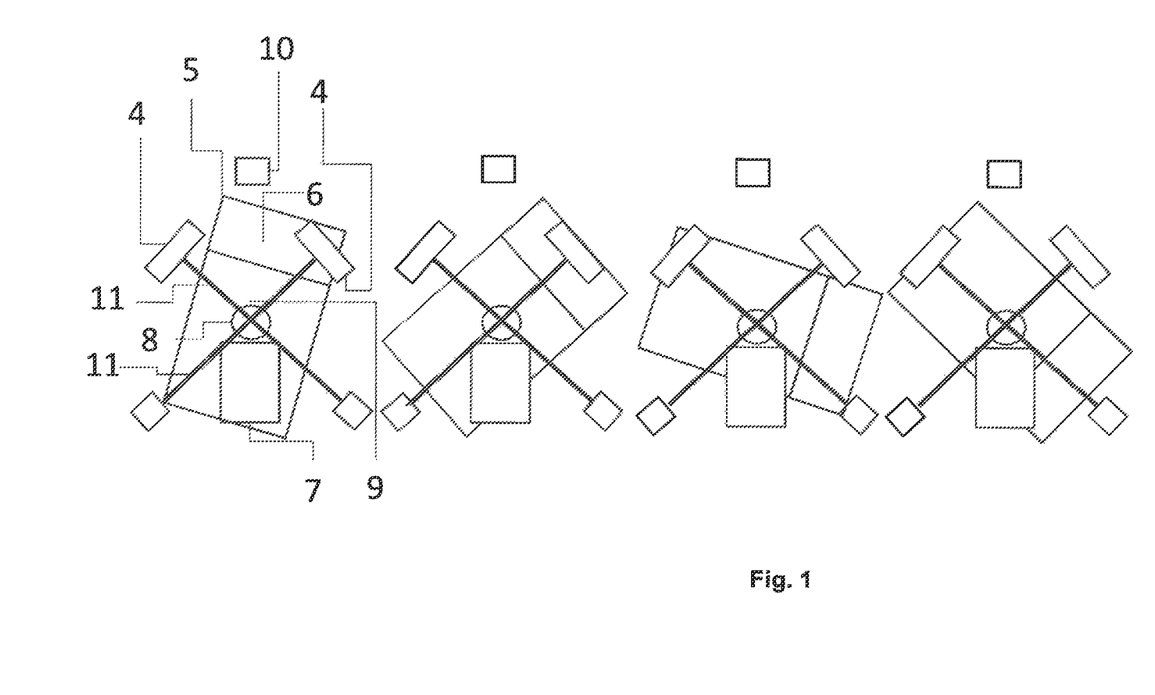
FIG. 1 illustrates a first embodiment of a medical system suitable to apply the present invention.

FIG. 1 shows a first embodiment of a medical system comprising a radiation treatment apparatus 5, the gantry of which is rotatable around a patient 8 lying on a patient support unit 7. The radiation treatment apparatus 5 comprises a treatment beam source 6 adapted to generate one or more treatment beams for irradiating a pathological structure of the patient's body 8. The surface section 9 of the patient's body 8 is spatially monitored by an optical camera system 10.

As soon as the patient's body 8 moves for whatever reason from its initial position, such motion will be detected by the camera system 10 since the surface section 9 will move correspondingly. For this, it is assumed that the pathological structure of the patient's body 8 has also moved from its intended position, meaning that the treatment beam may not be properly aligned with the pathological structure any more which may compromise the outcome of the treatment procedure.

Thus, it has to be checked in which direction and by which amount the pathological structure has moved, for which purpose image-guided radiotherapy utilizes x-ray images.

As the camera system 10 has not only determined that the patient body 8 has moved, but also has determined—by comparison of the initial spatial position of the surface section 9 and the spatial position in which the surface section 9 has come to rest again—in which direction the patient's body 8 has moved, an optimum spatial direction for a check x-ray image can be calculated, that is ideally perpendicular to the direction the patient's body 8 and presumably also the pathological structure has moved in.

As can be seen in FIG. 1, the medical system comprises two x-ray imaging devices 4 having lines of sight 11 which, in the shown embodiment, intersect each other at an almost right angle. Knowing the spatial direction the patient's body 8 has moved in as well as the spatial directions of the respective lines of sight 11, the x-ray imaging devices 4 can be controlled in such a manner that a check x-ray image is acquired along the line of sight 11 which is most perpendicular to the direction of motion of the patient's body 8. According to the present invention, a check x-ray image is always acquired by the x-ray imaging device 4 which his most suitably aligned with respect to the direction of motion of the patient's body 8. Consequently, the x-ray image acquired is the most suitable one for quantifying the spatial deviation of the patient's body 8 along with the pathological structure.

Based on the pathological structure's spatial position derived from a planning scan and its spatial position derived from the check x-ray image, the actual positional deviation can be calculated and compensated for during the remaining radiotherapy treatment procedure. For example, the treatment beam(s) can be rearranged with respect to the pathological structure, for example by re-configuring the collimator of the treatment beam source 6, or by repositioning the patient support unit 7 together with the patient's body 8 with respect to the radiation treatment apparatus 5 and the treatment beam(s).

Figure 2:
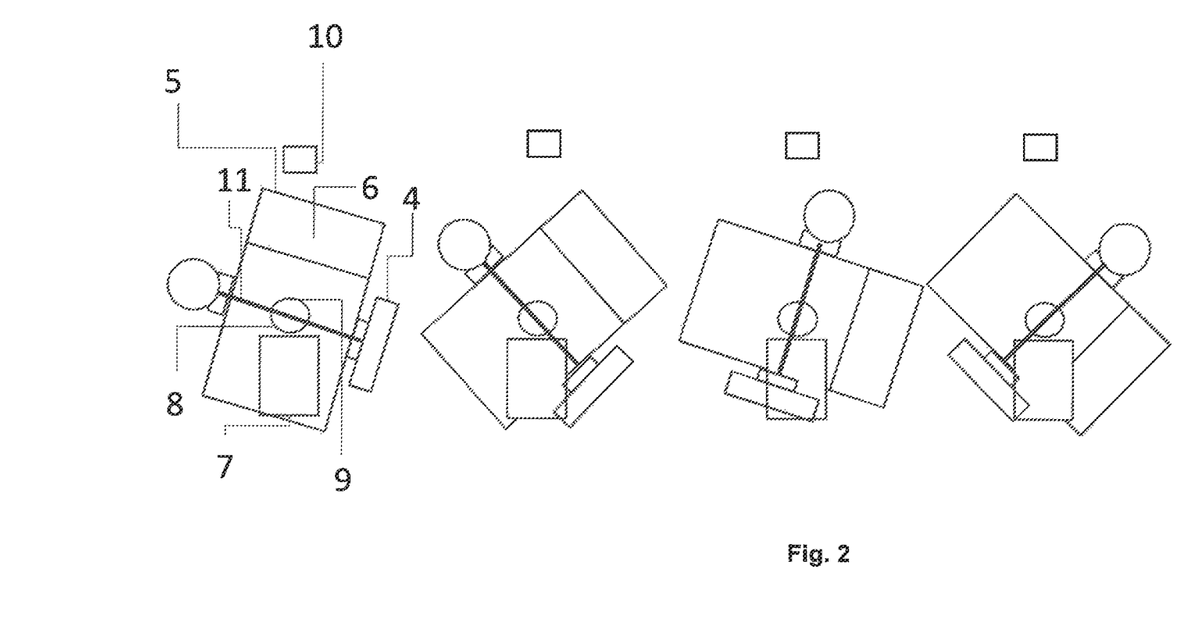
FIG. 2 illustrates a second embodiment of a medical system suitable to apply the present invention.

FIG. 2 shows a second embodiment of a medical system having a radiation treatment apparatus 5, which differs from the first embodiment shown in FIG. 1 in that it comprises a single x-ray imaging device 4 which is provided at the gantry of the radiation treatment apparatus 5 and therefore correspondingly rotates around the patient's body 8 during a radiotherapy procedure. If a motion of the patient's body 8 occurs and the direction thereof has been calculated with the help of the camera system 10, the x-ray imaging device 4 can be controlled to acquire the desired check image once the line of sight 11 reaches a position in which it is most perpendicular to the direction of motion. In a specific example during a radiotherapy procedure, the treatment beam could be "paused" once a positional deviation of the patient's body 8 has been determined, but with the gantry continuing its rotational motion around the patient's body. Once the line of sight 11 of the x-ray imaging device 4 has reached its optimum spatial direction and a check x-ray image has been acquired, the gantry could be reversed to its former position where the treatment beam has been paused in order to then continue radiotherapy. In the alternative, the treatment beam can be activated even when the gantry is reversed to its former position to apply the omitted radiation dose. In an embodiment having a plurality of x-ray imaging devices 4, it can be determined which x-ray imaging device reaches the optimum spatial direction or will come closest to the optimum spatial direction first. With the gantry continuing its normal motion, the x-ray acquisition can be triggered once the corresponding x-ray imaging device has reached the determined position that provides the best outcome.

Figure 3:
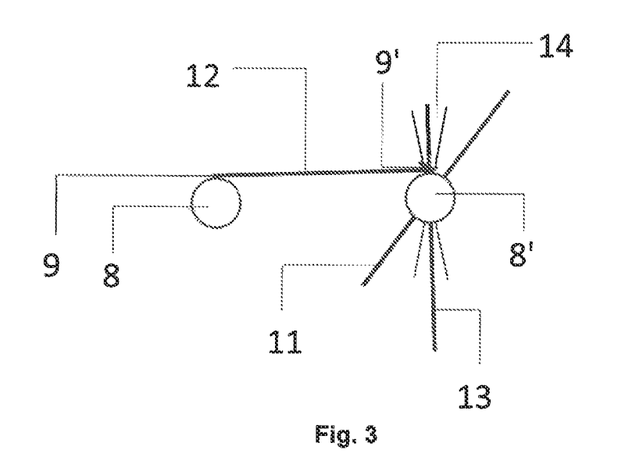
FIG. 3 schematically illustrates the inventive approach for monitoring the spatial position of a patient's body part.

FIG. 3 schematically explains the geometric principles of the inventive approach: In the shown example, the patient's body 8 along with the pathological structure may move in a lateral direction to the right and come to rest again at position 8'. With a spatial position of the surface section 9 being monitored over time, the spatial direction 12 can be calculated by comparison of the images received via the camera system 10. Since a check x-ray image provides the best result if it's image plane substantially contains the spatial direction of motion 12, an optimum spatial direction 13 is calculated as being perpendicular to the spatial direction 12. As for some cases the optimum spatial direction 13 cannot be reached by an x-ray imaging device at all or not fast enough to ensure a time efficient radiotherapy procedure, a range of acceptance 14 can be defined around the optimum spatial direction 13, within which a triggered check x-ray image will still provide still satisfying results for quantifying the motion of the pathological structure.

Figure 4:
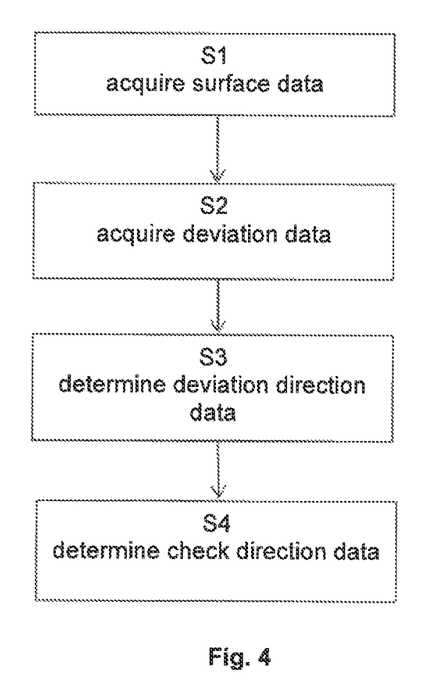
FIG. 4 illustrates the basic method steps according to the present invention.

FIG. 4 shows the basic steps of the inventive approach: once the spatial position of a surface section 9 of the patient's body part 8 has been determined (S1), it can also be determined when a deviation of this spatial position occurs (S2). Based on a comparison of images provided by the camera system 10, the spatial direction in which the deviation/motion has occurred can be determined (S3), which in turn serves as the basis for determining the optimum spatial direction in which a check x-ray image provides the most valuable image data (S4).

Figure 5:
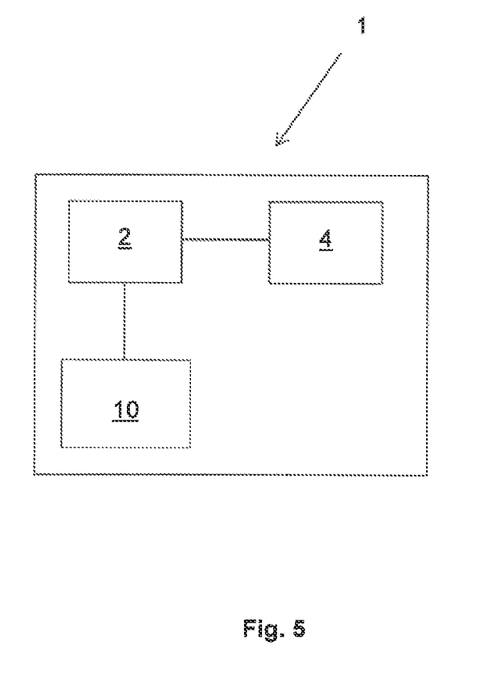
FIG. 5 schematically illustrates a system according to the fifth aspect of the present invention.

FIG. 5 is a schematic illustration of the medical system 1 according to the fifth aspect. The system is in its entirety identified by reference sign 1 and comprises a computer 2, an optical camera 10 adapted for performing surface measurements of the patient's surface, and an x-ray device 4 for acquiring one or more check x-ray images. The components of the medical system 1 have the functionalities and properties explained above with regard to the fifth aspect of this disclosure.

The invention claimed is:

1. A computer-implemented medical method for monitoring a spatial position of a patient's body part, wherein the method comprises the following steps:
    acquiring surface data describing a spatial position of at least a surface section of the patient's body part;
    acquiring deviation data based on the surface data, describing that the spatial position of the surface section deviates from a target spatial position for the surface section;
    determining deviation direction data based on the surface data and the deviation data, describing a spatial direction in which the spatial position of the surface section deviates from the target spatial position for the surface section; and
    determining check direction data based on the deviation direction data, describing at least one optimum spatial direction for a line of sight of a check x-ray-image that qualifies for quantifying a deviation of the spatial position of the patient's body part from a target spatial position for the patient's body part, the at least one optimum spatial direction being substantially perpendicular to the spatial direction in which the spatial position of the surface section deviates from the target spatial position.

2. The method according to claim 1, wherein acquiring surface data involves monitoring the spatial position of the surface section via at least one camera adapted for optical surface measurements, and particularly involves at least one of:
    a time-of-flight measurement;
    a structured-light measurement; or
    a stereoscopic measurement.

3. The method according to claim 1, wherein the spatial direction in which a deviation of the spatial position of the surface section from the target spatial position for the surface section is determined, includes at least one of a direction of a translational deviation and/or an axis of rotation of a rotational deviation.

4. The method according to claim 1, wherein the optimum spatial direction is defined as being:
    substantially perpendicular to the direction of a translational deviation, and/or
    substantially parallel to the axis of rotation of a rotational deviation.

5. The method according to claim 1, wherein determining check direction data involves determining a range of acceptance around the at least one optimum spatial direction, defining an upper limit for an angle enclosed by the optimum spatial direction and an acceptable spatial direction for a line of sight of a check image.

6. The method according to claim 1, further including the following steps:
    acquiring imager direction data describing the current spatial direction of a line of sight of an x-ray imaging device which is adapted to provide the check image;
    generating, based on the check direction data and the imager direction data, a triggering signal for the x-ray imaging device to acquire a check image in the optimum spatial direction or at least within the range of acceptance.

7. The method according to claim 6, wherein the x-ray imaging device comprises a plurality of x-ray imaging devices.

8. The method according to claim 7, wherein the plurality of x-ray imaging devices have lines-of-sight that intersect each other at an angle.

9. The method according to claim 6, wherein the x-ray imaging device is movable with respect to the patient's body part along a circumferential pathway around the patient's body part together with a radiation treatment apparatus.

10. The method according to claim 6, wherein the step of generating a triggering signal includes selecting, from a plurality of x-ray imaging devices, an x-ray imaging device the line of sight of which is closest to, is within or will at first reach the optimum spatial direction or at least the range of acceptance.

11. The method according to claim 6, wherein generating the triggering signal further depends on at least one of:
    relative position between a radiation treatment apparatus and the patient's body part;
    dose of radiation applied to the patient's body part; or
    elapsed radiation treatment time.

12. The method according to claim 6, wherein generating the triggering signal includes changing the relative position of the patient's body part and the x-ray imaging device such that the line of sight of the x-ray imaging device substantially coincides with the optimum spatial direction or is at least within the range of acceptance.

13. The method according to claim 12, wherein generating the triggering signal includes changing the relative position of the patient's body part and the x-ray imaging device includes moving at least one of a patient support unit and the x-ray imaging device.

14. A non-transitory computer readable medium storing instructions thereon, that when executed by a computer, cause the computer to perform a method comprising the steps of:
    acquiring surface data describing a spatial position of at least a surface section of the patient's body part;
    acquiring deviation data based on the surface data, describing that the spatial position of the surface section deviates from a target spatial position for the surface section;
    determining deviation direction data based on the surface data and the deviation data, describing a spatial direction in which the spatial position of the surface section deviates from the target spatial position for the surface section; and
    determining check direction data based on the deviation direction data, describing at least one optimum spatial direction for a line of sight of a check x-ray-image that qualifies for quantifying a deviation of the spatial position of the patient's body part from a target spatial position for the patient's body part, the at least one optimum spatial direction being substantially perpendicular to the spatial direction in which the spatial position of the surface section deviates from the target spatial position.

15. A medical system, comprising:
    a) at least one computer configured to perform a method including:
        acquiring surface data describing a spatial position of at least a surface section of the patient's body part;
        acquiring deviation data based on the surface data, describing that the spatial position of the surface section deviates from a target spatial position for the surface section;

determining deviation direction data based on the surface data and the deviation data, describing a spatial direction in which the spatial position of the surface section deviates from the target spatial position for the surface section; and determining check direction data based on the deviation direction data, describing at least one optimum spatial direction for a line of sight of a check x-ray-image that qualifies for quantifying a deviation of the spatial position of the patient's body part from a target spatial position for the patient's body part, the at least one optimum spatial direction being substantially perpendicular to the spatial direction in which the spatial position of the surface section deviates from the target spatial position;

b) a camera adapted for optical surface measurements; and c) a x-ray imaging device for providing at least one x-ray-check image of the patient's body part, wherein the at least one computer is operably coupled to the camera for determining check direction data; and the x-ray imaging device for issuing a control signal to the x-ray imaging device for controlling the operation of the x-ray imaging device on the basis of the check direction data.

16. The system according to the claim 15, further comprising a radiation treatment apparatus comprising a treatment beam source and a patient support unit, wherein the at least one computer is operably coupled to the x-ray imaging device for issuing a control signal to the x-ray imaging device for controlling, on the basis of the check direction data, at least one of the operation of the x-ray imaging device or the position of the patient support unit.

* * * * *